United States Patent [19]
Smith et al.

[11] Patent Number: 5,834,006
[45] Date of Patent: Nov. 10, 1998

[54] LATEX-BASED AGRICULTURAL COMPOSITIONS

[75] Inventors: Geoffrey W. Smith, Buckland; Patrick J. Mulqueen, Abingdon; Eric S. Paterson, Wantage; John Cuffe, Heacham, all of Great Britain

[73] Assignee: Dow AgroSciences LLC, Indianapolis, Ind.

[21] Appl. No.: 790,729

[22] Filed: Nov. 8, 1991

Related U.S. Application Data

[63] Continuation of Ser. No. 469,427, Apr. 5, 1990.

[51] Int. Cl.⁶ .................................................. A01N 25/08
[52] U.S. Cl. ........................................... 424/409; 504/118
[58] Field of Search ................................ 424/405, 78.06, 424/409; 514/532

[56] References Cited

U.S. PATENT DOCUMENTS

| | | | |
|---|---|---|---|
| 3,400,093 | 9/1968 | Feinberg . | |
| 4,304,769 | 12/1981 | Chen ....................................... | 424/218 |
| 4,323,602 | 4/1982 | Parker ..................................... | 427/298 |
| 4,818,536 | 4/1989 | Meyers et al. .......................... | 424/407 |
| 4,954,338 | 9/1990 | Mattox .................................... | 424/405 |

FOREIGN PATENT DOCUMENTS

| | | |
|---|---|---|
| 0708798 | 1/1968 | Belgium . |
| 3304457 | 10/1983 | Germany . |
| 58-072501 | 4/1983 | Japan . |
| 0658222 | 5/1949 | United Kingdom . |
| 1367137 | 8/1971 | United Kingdom . |
| 2072506 | 2/1981 | United Kingdom . |
| 2138291 | 10/1984 | United Kingdom . |

OTHER PUBLICATIONS

Dial Index Abstracts—"Chlorpyrifos–Methyl"—Bifenox—Prochlorog . . . Muarimol—Fluroxypyr.

Basic Abstracts Journal, Section C, week K23, 3 Aug. 1983, No. 55173, Derwent Publications.

*Primary Examiner*—Peter F. Kulkosky
*Attorney, Agent, or Firm*—Donald R. Stuart

[57] ABSTRACT

An agricultural composition, for example, a herbicidal, insecticidal or fungicidal composition, comprising at least a first active pesticidal component, and at least one other active component, the other active component being physico-chemically, chemically, or biologically incompatible with the first pesticidal component. The composition is in the form of a latex dispersion, containing at least one emulsifying surfactant and having a continuous aqueous phase, and at least a first dispersed phase. The first dispersed phase contains particles derived from a latex, and the first pesticidal component is present in the composition substantially wholly within the first dispersed phase. The said other active ingredient is present within the continuous phase, or within a second dispersed phase.

7 Claims, No Drawings

LATEX-BASED AGRICULTURAL COMPOSITIONS

CROSS-REFERENCE TO RELATED APPLICATION

This is a continuation of application Ser. No., 07/469,427 filed Apr. 5, 1990

This invention relates to agricultural compositions, and in particular to herbicidal, fungicidal, and insecticidal compositions (hereinafter referred to as pesticidal compositions), for a variety of pre and post-emergence applications.

It is generally desired of such pesticidal compositions that they should be easy to handle, and to apply in any desired concentration. Pesticidal compositions are generally supplied in a variety of forms, for example, as wettable powders, emulsifiable concentrates, and suspension concentrates. Such types of formulation have application for a wide range of active ingredients.

It is often desirable to incorporate two active components into a single agricultural composition. Thus, for example, it will often be desirable to incorporate together two different types of insecticide, or two different types of herbicide, in order to obtain a broader spectrum of activity. Also, it is frequently desired to incorporate different types of pesticide within the same composition, for example, to formulate a fungicide with a herbicide, or a fungicide with an insecticide. Attempts to formulate such compositions containing two active ingredients can give rise to substantial difficulties because of various types of incompatibility between the active substances employed. Examples of different types of incompatibility are the following:

(a) physico-chemical incompatibility
(b) chemical incompatibility
(c) biological incompatibility (often evidenced as a phytotoxic response).

(a) Examples of physico-chemical incompatibility are the following:

1. From a biological standpoint, a mixture of fluroxypyr (as 1-methyl heptyl ester) with chlortoluron is attractive. Fluroxypyr 1-methyl heptyl ester is an organosoluble product with a melting point of about 56° C., usually formulated as an emulsifiable concentrate. Chlortoluron is a high melting point product normally formulated as an aqueous suspension concentrate. When attempts are made to produce a suspension concentrate of the mixture, by milling both components together in an aqueous medium, a melting point depression is observed rendering the formulation unstable.

2. Again, from a biological standpoint, it is often desirable to attempt to mix chemicals which are either oils or low melting point solids of appreciable organic solvent solubility with solids of high melting point and low organic solvent solubility. This technique of preparing suspension-emulsions is very difficult due mainly to the problem of preventing transfer of material between phases resulting in gross physical changes or chemical instability. Some advances have been made in this area, as exemplified by European Patent Application No. 0117999 which describes the use of phthalate esters as solvents to produce acceptable formulations. This disclosure is however restricted to a limited range of pesticides since the pesticide must be compatible with phthalate esters.

3. The problem of mixing a non-aqueous phase with an electrolyte solution is one often addressed by the pesticide formulator and although specific products can be produced to be compatible with electrolytes, these are often so finely balanced in terms of emulsion performance that the product does not perform well in dilution in the natural water of a spray-tank. This difficulty is especially true with liquid fertilizer applications but also in the case of mixing one pesticide active as a salt solution with an oil-solution of another pesticide and attempting to produce a stable mixture therefrom.

4. When chemicals interact to produce melting point depressions, if that melting point depression is large the resultant mixed melting point product can sometimes be formulated in the same way as a low melting point single component but there still remains the problem of formulating this new oil-phase with a solid phase. This cannot easily be achieved using conventional technology.

(b Examples of chemical incompatibility of components are very many but can be illustrated by the following:

Chlorpyrifos-methyl is an organo-phosphate pesticide which has shown an improved spectrum of activity when sprayed with another type of pesticide, the insect growth regulators, the acyl areas. One of this group, [1-3,5-dichloro-4-(1,1,2,2-tetrafluoroethoxy)phenyl]-3-(2,6-difluorobenzoyl) urea, referred to herein as "Active N" is highly active in combination with chlorpyrifos-methyl. Active N is only poorly organo-soluble, necessitating the use of potent solvents, e.g., N-methyl pyrrolidone in order to achieve oil solution of both chlorpyrifos-methyl and Active N. In such solutions, however, there is a chemical incompatibility between chlorpyrifos-methyl and Active N resulting in the ester hydrolysis of chlorpyrifos-methyl. Other methods are therefore required to achieve such mixed products.

(c) Examples of biological incompatibility are usually those where mixtures of products demonstrate lack of efficacy (often traced back to a chemical or physico-chemical incompatibility) or where mixtures of products show increased unacceptable crop damage (phytotoxicity). An example of this is a mixture of bifenox with a non-aqueous solvent, when applied to cereals. Bifenox in combination with most non-aqueous solvents (sometimes just in combination with surfactant) is usually unacceptably phytotoxic. Therefore it is desirable to provide a method of lowered phytotoxicity when mixing a product such as bifenox with a herbicide soluble in non-aqueous solvents, designed to broaden its spectrum of activity.

Naturally, some pesticide mixtures will display more than one of the problems outlined above but these are all problems necessary to be overcome by the formulation chemist in order to prepare marketable pesticide formulations.

European Patent Specification No. 0080516, discloses insecticidal compositions in which the active substance is incorporated within particles of a latex and that thereby waterborne dispersions may be prepared. These prior art disclosures are, however, restricted to the use of specific insecticides, chlorpyrifos and chlorpyrifos-methyl, and the disclosure indicates that it is essential that the pesticide utilized is either a liquid or a low-melting solid at ambient temperatures, so that it can be solubilized into the polymer at temperatures less than 100° C. as a liquid. Furthermore the disclosure does not indicate that such use of latex-containing pesticidal formulations can eliminate incompatibilities between otherwise incompatible active ingredients.

Furthermore, although the method disclosed in EP 0080516 enables the preparation of latex-containing compositions of chlorpyrifos, its method requires that the active substance should be heated to 60° C. for 2 hours. This is both inconvenient to carry out industrially, and can give rise to thermal degradation of the chlorpyrifos.

In addition the method is very unsatisfactory with pesticides which have a somewhat higher melting point.

GB-A-2072506 (Desowag-Bayer) is concerned with a film-forming wood preservative concentrate substantially free of inorganic salts or pigments. The compositions disclosed therein comprise an insecticide or fungicide, a water insoluble solvent, and a water-dilutable aqueous plastics dispersion which may be a polymer or copolymer of a vinyl ester, an acrylic acid ester, or a methacrylic acid ester. The compositions also comprise from 0 to 2% of an emulsifier. Although the compositions are somewhat dilutable in water (up to 1:4), the compositions are not in the nature of suspension concentrates, i.e., ones which are essentially infinitely diluable (particularly dilutable up to at least 50:1) in water. This is not surprising when it is considered that the essential characteristic of the compositions of the reference is that they contain drying oils and/or an alkyd resin. They are thus in the nature of paints, for application to timber and the like and the purpose of the latex in the composition is to act as a film-former.

It is inconsistent with the latex acting as film-former that high levels of surfactant should be present, and in particular that a sufficient amount of surfactant should be present to enable the compositions to be essentially infinitely dilutable with water). It is well known that the presence of surfactants will interfere with the film forming properties of latex dispersions such as are described in GB-A-2072506, such that incomplete and non-adhesive deposits will be produced, and not the continuous adherent films which the Patentees seek to produce.

As in EP-A-0080516, GB-A-2072506 does not teach that the use of a latex in a pesticide composition is effective to improve compatibility of incompatible active materials.

GB-A-658222 (B.F. Goodrich) discloses pesticidal composition containing a latex of PVC or the like, to assist the active material to stick to the intended substrate. This patent is not however concerned with the preparation of stabilized concentrate solutions.

U.S. Pat. No. 3,400,093 (Feinberg) discloses insecticide-containing compositions including polymers and polymer latexes. The latexes are present in these compositions to improve their coating properties and the compositions are not like those of GB-A-207250 and GB-A-658222, and are not water-dilutable concentrates.

DE-A-3304457 (Toagosei Chem Ind (sic)) is concerned with the dispersion of solid pesticidal particles within a latex.

JP-A-8072-501 (Toa Gosei Chem Ind) is concerned with the preparation of what are effectively solutions of high molecular weight polymers, including pesticidal substances, which are obtained by the neutralization of an acid dispersion of a copolymer with an alkali. This reference is not concerned with the stabilization of pesticide-containing emulsions, using polymer latexes.

GB-A-2138291 (Tzang) is also concerned with the coating compositions in the nature of paints, containing insecticidally active ingredients. These compositions contain polymer latexes.

BE-A-708798 (Bayer) is similar in some ways in its disclosure to EP 0080516, in that it is concerned with insecticidal compositions, in which the insecticidal material can be directly imbibed into the particles of a latex for application purposes.

GB-A-1367137 (PVO International) is concerned with insecticidal compositions for mothproofing of wool. The aim of the invention is to improve the persistence of insecticides in a treated fabric, by holding the insecticidal material in place on the woollen subtrate, using a polymer, which has been polymerized in situ. This is achieved by applying the insecticidal material as a composition including a polymerizable resin. Such resins are, in some embodiments, used in the form of a latex.

None of these references address the problems of incompatibility between different active ingredients in pesticidal compositions.

We have now surprisingly discovered that incompatibility problems such as discussed above can largely be solved for many systems by formulating the composition in the form of a pesticide-containing aqueous latex dispersion wherein a first one of the active components is substantially wholly contained in a dispersed phase derived from a latex. The second different type of active component is not substantially wholly contained within this phase and is present as a dispersion and/or a solution in the continuous aqueous phase.

An agricultural composition, comprising at least a first active pesticidal component, and at least one other active component which is a second type of pesticidal component or a fertilizer, wherein the said at least one other active component is physico-chemically, chemically or biologically incompatible with the first pesticidal component, the composition being in the form of an aqueous dispersion having a continuous aqueous phase, and at least a first dispersed phase, wherein the composition comprises at least one emulsifying surfactant in an amount sufficient to render the composition water-dispersible, characterized in that the first dispersed phase contains particles derived from a latex, the said first pesticidal component is present in the composition substantially wholly within the said first dispersed phase, and in that the said other at least one active ingredient is essentially all present either in the continuous aqueous phase, or in a second dispersed phase, whereby the said incompatibility is reduced or eliminated.

The pesticide-containing latex dispersion may be produced by, for example, the method disclosed in EP 0080516 when the active substance has a suitably low melting point, e.g., 40° C. or lower. Alternatively and preferably the active substances may be dissolved in an appropriate water-immiscible solvent, and thus an oil-in-water emulsion of the resulting solution is formed. The emulsion is combined with a latex and the second active substance.

The term "particles" as used herein is not meant to carry with it any implication as to the physical state (i.e. liquid or solid) of the dispersed phase, and specifically is intended to include within its scope droplets comprising the pesticidal substance. It should also be understood that the term "water immiscible" as used herein is not intended to signify that the solvent is totally water-immiscible but only that the solvent is not freely miscible with water.

The term "latex" as used herein is intended to include any polymeric product produced as an aqueous suspension by an emulsion polymerisation process and includes within its scope both synthetic latexes and natural latexes.

The preferred latexes comprise polymers and copolymers of styrene, alkyl styrenes, isoprene, butadiene, acrylonitrile, lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, the size of the polymeric particles being in the range of from 0.03 to 20 microns, preferably from 0.1 to 10 microns. Small amounts, for example, 0–10% of bifunctional vinyl monomers may be employed to crosslink the polymers if desired.

Specifically, it has been discovered that particularly good results are obtained when the initial droplet size of the emulsion formed is from 1 to 100 microns, wherein the latex employed has a particle size of from 0.03 to 20 microns, and wherein the resulting dispersion formed has a particle size which lies between that of the initially-formed emulsion particles, and that of the latex particles. This can be determined by examining optically the average particle size of the dispersion formed, and noting optically the change of the particle size with time.

In general, it is found that an emulsion having a relatively large particle size (1 to 100 microns) is formed initially, but that the droplet size decreases with time. It is believed the latex combines with the emulsion droplets to produce a dispersion having a substantial number of particles with an intermediate particle size, for example, in the range of 0.03 to 20 microns, preferably from 0.1 to 10 microns, more preferably from 0.1 to 5 microns, more preferably still from 0.1 to 2 microns. Some individual droplets larger than these size ranges may also be present.

The first active pesticidal component may, preferably be dissolved in a water immiscible solvent prior to the initial emulsion formation, or if it has a sufficiently low melting point, it may be emulsified without the use of an organic solvent.

The latex may be present when the initial emulsion is formed, in which case the emulsion droplets will begin to combine with the latex immediately after they are formed. Alternatively, an emulsion may first be formed by combination of the solution of the pesticide with the emulsifier, in the presence of water, and the emulsion thus formed may thereafter be combined with the latex.

In order to form an initial aqueous dispersion of pesticide solution having the desired droplet size, it has been found necessary to employ an emulsifier (i.e. a surfactant). The emulsifier can be incorporated into the continuous (aqueous) phase, (in which case the surfactant preferably has a hydrophile-lipophile balance (HLB) number of 12 or more). Alternatively the surfactant may be incorporated into the dispersed phase (in which case the surfactant preferably has a HLB number of less than 12).

Surfactants which can be advantageously employed herein can be readily determined by those skilled in the art and include various nonionic, anionic, cationic or amphoteric emulsifiers, or a blend of two or more emulsifiers may be employed. The surfactant employed for the emulsification of the non-aqueous phase should be compatible with the latex and with any surfactants which may be present in the latex composition.

Examples of nonionic surfactants useful in preparing the oil-in-water emulsion include the polyalkylene glycol ethers and condensation products of alkyl phenols, aliphatic alcohols, aliphatic amines or fatty acids with ethylene oxide, propylene oxide or mixtures of ethylene and propylene oxides such as the ethoxylated alkyl phenols or ethoxylated aryl or polyaryl phenols and carboxylic esters solubilized with a polyol or polyoxyethylene. Cationic emulsifiers include quaternary ammonium compounds and fatty amines. Anionic emulsifiers include the oil-soluble (e.g. calcium, ammonium) salts of alkyl aryl sulphonic acids, oil soluble salts of sulphated polyglycol ethers, salts of the esters of sulphosuccinic acid, or half esters thereof with nonionic surfactants and appropriate salts of phosphated polyglycol ethers. Preferred emulsifiers are those which form and stabilize oil-in-water emulsions such as ethoxylated alcohols, alkoxylated alkyl phenols or polyalkylene oxide co-polymers. The surfactant is employed in an amount sufficient to ensure that the emulsion so formed prior to addition of a latex is easily formed and yet does not cause the latex to coagulate. This amount will be from 0.1 to 15.0% of the total composition, preferably 1.0% w/w to 10%.

The nature of the water-immiscible solvent, if present, used in the present invention will vary depending upon the pesticidal substance which it is desired to incorporate, and the latex type. Specific examples, however, are the aromatic liquids, particularly alkyl substituted benzenes such as xylene or propyl benzene fractions, and mixed naphthalene and alkyl naphthalene fractions; mineral oils, substituted aromatic organic liquids such as dioctyl phthalate; kerosene, polybutenes; dialkyl amides of various fatty acids, particularly the dimethyl amides of fatty acids such as the dimethyl amide of caprylic acid; chlorinated aliphatic and aromatic hydrocarbons such as 1,1, 1-trichloroethane and chlorobenzene, esters of glycol derivatives, such as the acetate of the n-butyl, ethyl, or methyl ether of diethylene glycol, the acetate of the methyl ether of dipropylene glycol, ketones such as isophorone and trimethyl cyclo-hexanone (dihydroisophorone) and the acetate products such as hexyl, or heptyl acetate. The preferred organic liquids are xylene, propyl benzene fractions, dihydroisophorone, and alkyl acetates.

Pesticidal substances suitable for use as the first pesticidal component in the composition in accordance with the invention include the following insecticides:

| | |
|---|---|
| allethrin | butocarboxim |
| amitraz | carbophenothion |
| azinphos-ethyl | carbosulfan |
| azinphos-methyl | chlordimeform |
| benfuracarb | chlorfenvinphos |
| benzoximate | chlormephos |
| bifenthrin | chlorobenzilate |
| binapacryl | chloropropylate |
| bioallethrin | chlorphoxim |
| bioresmethrin | chlorpyrifos |
| bromophos | chlorpyrifos-methyl |
| bromophos ethyl | crotoxyphos |
| bromopropylate | cyanophos |
| butocarboxim | cyfluthrin |
| cypermethrin | cyhalothrin |
| deltamethrin | ethiofencarb |
| demeton | ethion |
| demeton-S-methyl | ethofumesate |
| 1,3-dichloropropene | ethoprophos |
| dichlorvos | etrimfos |
| dicofol | fenamiphos |
| dinobuton | fenitrothion |
| dioxabenzofos | fenobcarb |
| dioxacarb | fenpropathrin |
| dioxathion | fenthion |
| disulfoton | fenvalerate |
| endosulfan | flucythrinate |
| EPN | fluvalinate |
| pirimiphos-methyl | fonofos |
| profenofos | furathiocarb |
| promecarb heptenophos | |
| propaphos | hydroprene |
| propargite | isofenphos |
| prothiofos | isoxathion |
| quinalphos | malathion |
| resmethrin | mecarbam |
| sulprofos | mephospholan |
| temephos | methacrifos |
| tetradifon | methidathion |
| tetramethrin | methoprene |
| thiocyclam | mevinphos |
| thiometon | naled |
| tralomethrin | parathion |
| triazophos | parathion methyl |
| xylylcarb | permethrin |

-continued phenothrin
phosalone
phosfolan
phosmet
phoxim

N-2,3-dihydro-3-methyl-1,3-thiazol-2-ylidene-2,4-xylidine.

The following fungicides:

| | |
|---|---|
| benalaxyl | dodemorph |
| bis-(2,4-dichlorophenyl ethyl phosphate | tridemorph |
| bupirimate | fenpropidin |
| buthiobate | fenpropimorph |
| carboxin | and other morphine |
| dodine | fungicides and ergosterol |
| edifenphos | biosynthesis inhibitors |
| etridiazole | such as |
| imazalil | bitertanol |
| iprobenfos | fenarimol |
| nuarimol | myclobutanil |
| oxycarboxin | penconazole |
| tolclofos-methyl | prochloraz |
| | triadimefon |
| | triadimenol |

The following herbicides:

| | |
|---|---|
| acetochlor | 2,4-D esters |
| alachlor | 2,4-DB esters |
| anilophos | di-allate |
| benfluralin | 2,4-DP esters |
| bensulide | diclofop-methyl |
| benzoylprop-ethyl | diethatyl |
| bifenox | dimethachlor |
| bromoxynil octanoate | dinitramine |
| butachlor | EPTC |
| butamifos | ethalfluralin |
| butralin | ethofumesate |
| butylate | fenoxaprop-ethyl |
| fluorochloridone | flamprop-methyl |
| chlorphropham | fluazifop butyl |
| clopyralid | fluchloralin |
| ethylhexyl ester | |
| cycloate | flumentralin |
| cycloxydim | fluorodifen |
| fluroxypyr-1-methyl heptyl ester | fluoroglycofen ethyl |
| fluroxypyr ester | flurecol-butyl |
| haloxyfop ester (methyl/ethbxyethyl) | oxadiazon |
| ioxynil octanoate | oxyfluorfen |
| isopropalin | pendimethalin |
| MCPA esters | phenisopham |
| MCPB esters | phenmedipham |
| CMPP esters | picloram esters |
| metolachlor | profluralin |
| molinate | propachlor |
| monalide | propanil |
| napropamide | pyridate |
| nitrofen | quizalafop-ethyl |
| trifluralin | sethoxydim |
| | triallate |
| | triclopyr esters |
| | tridiphane |

2-(4-(2-fluoro-4-bromophenoxy)phenoxy propionic acid esters and the resolved isomers 2-(4-((3-fluoro-5-(trifluoromethyl)-2-pyridinyl)oxy)phenoxy propanoic acid esters and their resolved isomers.

The first active component may be an organosoluble derivative of a pesticidal compound which is itself poorly organosoluble or insoluble, such as cyhexatin dodecylbenzene sulphonate.

The first pesticidal component may also be a compatible mixture of two such pesticidal substances, for example, a solution of one such substance in another, or a eutectic mixture of two such substances (e.g. a eutectic mixture of fluroxypyr 1-methyl heptyl ester with bifenox).

The compositions of the invention may also include optional adjuvants such as freezing point depressants preferably in amounts of 0–15%, flow aids to prevent caking or aid in the redispersion of bottom sediment preferably in amounts of 0–5%, thickening agents preferably in amounts of 0–3% and defoamers preferably in amounts of 0–1% to improve the overall properties under field storage and use conditions.

Similarly conventional pesticide adjuvants such as solvents, surfactants for increasing penetration of the active substances or salts may be incorporated into the compositions to maintain or improve biological efficacy of the composition. These may be incorporated into the oil phase or aqueous phase as appropriate, typically in amounts of from 0 to 50% by weight.

The compositions of the invention may be prepared by first preparing an oil-in-water emulsion and subsequently adding a polymer latex dispersion, with stirring at a temperature from 0° C. to 100° C., preferably from 10° C. to 80° C., more preferably from 20° C. to 50° C.

The oil phase may contain from 10 to 80% w/v of the pesticide, preferably 10 to 60% and most preferably 20 to 50% w/v. The latex content of the composition will depend upon the latex type as well as the pesticide and surfactant type but may vary from 5 to 80% w/v, preferably 5 to 60% w/v and most preferably 10 to 50% w/v.

The emulsion may be prepared prior to addition of the polymer dispersion or by addition of the solution of the pesticide in the non-aqueous solvent to the polymer dispersion. A variety of stirring methods may be employed, from simple shaking, stirring through to sonication and high shear emulsification, including bead milling. The method employed, the temperature chosen and the time taken for equilibration will depend upon a) the nature and amount of the pesticidal compound and solvent employed.

b) the nature and amount of latex employed.

c) the nature and amount of surfactant employed.

The second different type of active component may be, for example, a water soluble component which is present in the aqueous phase of the resulting composition. The second active component is preferably a pesticide, for example, a pesticide which is intrinsically water soluble, or a water-soluble salt derivative such as a salt of an otherwise water-insoluble pesticide.

Examples of such second different type of active pesticide components which are either water-soluble or have water soluble-salts include the insecticides:

acephate
cartap
omethoate
oxamyl

The fungicides:

bronopol
dichlorophen
dimethirimol
dodemorph
dodine
fenpropimorph
quazatine
tridemorph
(±) 1-amino propyl phosphonic acid

--- acifluorfen
alloxydim
amitrole
ammonium sulphamate
asulam
benazolin
bentazone
bromoxynil
clopyralid
2,4-D
dalapon
2,4-DB
2,4-DES
dicamba
dichlorprop
difenzoquat
diquat
endothal
fenprop
fomesafen
glufosinate
glyphosate
imazapyr
imazaquin
ioxynil
MCPA
MCPB
CMPP
paraquat
picloram
triclopyr The plant growth regulators:

| chlormequat | ethophon |
| chlorphonium | mepiquat |
| daminozide | piproctanyl |

The second different type of active component may also be, for example, a water insoluble (or poorly water soluble) pesticide or mixture of pesticides present as a particulate dispersion in the aqueous phase. Examples of such second different type of active pesticide components include the insecticides:

bendiocarb
binapacryl
carbaryl
carbofuran
chlormethiuron
clofentezine
cyhexatin
diflubenzuron
gamma-HCH
hexythiazox
trichlorfon teflubenzuron and other acylurea insecticides such as chorfluazuron, and "Active N" referred to above.

The fungicides:

| anilazine | iprodione |
| anthraquinone | 3-isopropoxy-o-toluanilide |
| captafol | mancozeb |
| captan | ofurace |
| carbendazim | copper oxinate |
| chlorothalonil | pencycuron |
| copper oxychloride | thiabendazole |
| cyprofuram | thiophanate methyl |
| dichlofluanid | thiram |
| dichlobutrazol | |
| dichloran | |
| dithianon | |
| ethirimol | |
| fentin | |
| flutriafol | |
| hexaconazole | |

The herbicides:

aclonifin
ametryn
atrazine
aziprotryne
bifenox
chloridazon
chlorotoluron
chlorosulfuron
cynazine
difenoxuron
diflufenican
diuron
fluometuron
isoproturon
isoxaben
karbutilate
lenacil
metamitron
metazachlor
methabenzthiazuron
metoxuron
metribuzin
metsulfuron
neburon
proglinazine ethyl
promethryne
propazine
simazine Certain active substances may be present either in the first dispersed phase, or in the continuous phase depending on the formulation type. For example, esters of 2,4-D are soluble in organic solvents, and thus suitable for incorporation into the first dispersed phase. Its sodium salt is water-soluble and suitable for incorporation as the second different type of active component dissolved in the aqueous continuous phase.

In certain circumstances, it is even possible for the same pesticidal substance to be contained within both the first and the second different type of active components. For example, fluroxypyr 1-methyl heptyl ester forms a eutectic mixture in a 3:1 ratio mixture with bifenox. It is however not normally possible to incorporate further bifenox to make a storage-stable preparation, without the use of substantial quantities of organic solvents, which give rise to phytotoxicity.

Thus, in one embodiment, the first pesticidal component is a eutectic mixture of first and second pesticidal substances (for example fluroxypyr 1-methyl heptyl ester and bifenox), and the second component is a solid phase of one of the said substances, dispersed in the aqueous phase (for example dispersed bifenox).

The compositions of the invention may be produced by the preparation of a latex dispersion containing the first active component by a variety of means as discussed earlier, followed by blending with an aqueous solution or dispersion of the second active component. The aqueous dispersions of this second active or mixture of components may be prepared by the many techniques known in the art such as sand milling, bead milling and dry milling followed by dispersion in water. Such aqueous dispersions generally contain a surfactant system composed of a wetting agent and a dispersing agent or a combined wetter/dispersing agent, a suspension/flow and optionally an antifreeze agent and an antifoam agent. The levels of all such additives may be adjusted dependent upon the ratio of latex containing first pesticide phase to second active.

The range and choice of adjuvants is well known to those skilled in the art but as general examples the wetting agents employed may be an alkali metal salt of a phosphate partial ester of a ($C_6$–$C_{24}$) alkyl polyglycol ether (containing 2–20 EO units), an alkali metal salt of an alkyl naphthalene sulphonic acid or a nonionic polyglycol ether. The dispersing agents can be alkali metal or amine salts or sulfosuccinic acid half-esters, amine salts of phosphate partial esters of polyaryl phenol polyglycol ethers, alkali metal lignin sulfonates or condensation products of formaldehyde and cresols. Small quantities of an aluminium silicate having a lamellar structure of the bentonite type, such as, for example, Hectorite or montmorillonite may be added as a thickener with or without small quantities of a polysaccharide such as, for example, Rhodopol 23. Antifreeze agents may include ethylene glycol, propylene glycol or glycerol. The aqueous solutions may be prepared by simple dissolution of a water-soluble chemical in water or by neutralization of an acid with an appropriate base or by neutralization of a base with an appropriate acid. The aqueous continuous phase may contain active substances both dispersed in it and dissolved in it resulting in a three phase pesticide system for the product of the invention.

As discussed earlier the first and the second different type of pesticide components may be physico-chemically incompatible, chemically incompatible or biologically incompatible.

They also have the ability, since they contain film forming latexes in many cases, to be utilized in those areas where film forming is a desirable effect, such as in seed treatments and pest control usage in dwelling places. The invention is illustrated by the following examples which are not limiting but merely illustrative:

The following list identifies the various starting materials used in the Examples.

|   | Common Name | Trade Mark |
|---|---|---|
| | ACTIVES | |
| A | chlortoluron | DICURANE |
| B | chlorpyrifos-methyl (technical) | RELDAN |
| C | myclobutanil | SYSTHANE |
| D | prochloraz | SPORTAK |
| E | fluoroxypyr 1-methyl heptyl ester | STARANE |
| F | isoproturon | ARELON |
| G | bifenox | MODOWN |
| H | fenpropimorph | |
| I | ioxynil octanoacetate | |
| J | copper oxinate | |
| K | anthraquinone | |
| L | nuarimol | |
| M | (±)-1-aminopropyl phosphonic acid | |

-continued

|   | | |
|---|---|---|
| N | 1-[3,5-dichloro-4-(1,1,2,2-tetrafluoroethoxy)phenyl]-3-(2,6-difluorobenzoyl)urea | |
| | SURFACTANTS | |
| A | ethoxylated alcohol | ATLOX 4991 |
| B | ethoxylated alcohol blend | ATLOX 4896 |
| C | acrylic graft copolymer | ATLOX 4913 |
| D | phosphate ester | AGRILAN TKA125 |
| E | block copolymer | AGRILAN F502 |
| F | anionic ether sulphate | SOPROPHOR 4D384 |
| G | polyaryl phenol ethoxylate | SOPROPHOR BSU |
| H | half ester sulphosuccinate | PESTILISER B |
| I | ethoxylated tallow amine | ETHOMEEN T25 |
| J | block copolymer | PLURIOL PE6100 |
| K | block copolymer | PLURIOL PE 6200 |
| L | phosphate ester | SOPROPHOR FL |
| M | polycarboxylate | AGRILAN F460 |
| N | block copolymer | TENSIOFIX 35600DL |
| | SOLVENT | |
| A | xylene | |
| B | aromatic C9 benzenoid distillate | SOLVESSO 100 |
| C | hexyl acetate | EXXATE 600 |
| D | mixed naphthalene fraction | SOLVESSO 200 |
| E | fatty acid dimethylamide | HALCOMID M-8-10 |

| | POLYMER LATEXES TRADEMARK | | |
|---|---|---|---|
| Type | | Trade Mark | Particle Size (Microns) |
| A | terpolymer | VINAMUL 3452 | 0.1–0.3 |
| B | styrene butylacrylate | DOW LATEX DL420 | 0.12–0.15 |
| C | styrene butadiene | DOW LATEX DL893 | 0.14–0.2 |

EXAMPLE I

Preparation of a mixed formulation of fluroxypyr 1-methyl heptyl ester and chlorotoluron Active E (142 g) was dissolved in xylene (150 g) to produce a 48.6% w/w ester solution. 300 g of polymer latex B was added to 10 g of surfactant I to produce a homogeneous dispersion. 292 g of the ester solution was added to the latex/surfactant dispersion with high shear stirring and stirred for 30 minutes. 121 g of this pesticide-containing latex dispersion was added to a previously prepared 600 g/L chlorotoluron (Active A) suspension concentrate (800 g) and homogenized with high shear mixing. The product was then diluted to 1 liter with water. On storage at 40° C., this product did not solidify but remained a stable mixed suspension concentrate.

EXAMPLE IA (COMPARATIVE)

Active E (330 g) was dispersed in water (500 g) containing surfactant E (14.0 g) and propylene glycol (25 g). This dispersion was bead milled until the particle size of the suspension was about 3,0 microns (vmd) by Coulter Counter TA II (Coulter Counter is a Trade Mark). The product was diluted to 1 liter with water. 100 g of this milled product was added to 960 g of a commercial suspension concentrate of Active A and the product homogenized with a high-shear mixer. This product on storage solidified at 40° C. owing to a melting-point endotherm between fluroxypyr 1-methyl heptyl ester and chlorotoluron and was thus unacceptable.

EXAMPLE II

Preparation of a mixed formulation of fluroxypyr 1-methyl heptyl ester, ioxynil octanoate and isoproturon Active E (45 g) and active I (84 g) were dissolved in solvent B (100 g) and mixed with 10 g surfactant F. This oil phase was added to a latex dispersion prepared by mixing a ternary latex (latex A) (230 g) and water (30 g) and stirred with high shear mixing for 30 minutes. This aqueous pesticide containing latex dispersion (500 g) was added to a commercial isoproturon aqueous suspension concentrate (active F) (580 g) and mixed for 5 minutes. This product on storage at both 40° C. and 54° C. showed no crystal growth or emulsion growth after a period of 3 months storage as evidenced by Coulter Counter examination and microscopic evaluation, indicating a physically stable product.

EXAMPLE IIA (COMPARATIVE)

Active E (45 g) and active I (84 g) were dissolved in solvent B (100 g) and mixed with surfactant F (10 g). This oil phase was then emulsified into water (240 g) and the prepared emulsion mixed under high shear mixing with a commercial isoproturon aqueous suspension concentrate (580 g) (active F). The product was then diluted with water to 1 liter (approx 25 g). This product on storage at 45° C. and 54° C. showed crystal growth and emulsion growth after 1 months storage as evidenced by Coulter Counter examination and microscopic evaluation indicating a physically unstable mixture.

EXAMPLE III

Preparation of a mixed formulation of fluroxypyr 1-methyl heptyl ester and bifenox A solution was prepared of 300 g of active E a mixture of solvent D (240 g) and solvent E (60 g). This 50% w/w technical fluroxypyr ester solution (454.5 g) was stirred into a latex/surfactant dispersion prepared by mixing latex C (454.5 g) with 10 g of surfactant I and 122.6 g water. The mixture was stirred under high shear for 30 minutes. 260 g of this aqueous pesticide containing latex dispersion was added to 416 g of a commercial aqueous suspension of bifenox (active G) and diluted with water (104 g) to produce a stable mixed formulation containing 50 g/L fluroxypyr acid equivalent and 250 g/L bifenox.

EXAMPLE IIIA (COMPARATIVE)

A solution of 89 g fluroxypyr 1-methyl heptyl ester (active E) was prepared in a mixture of 120 g of solvent D with 27 g of solvent E.

This solution was emulsified into water (320 g) containing surfactant F (15 g) with a high shear mixer and the resultant emulsion mixed with a commercial bifenox aqueous suspension concentrate (493 g) (active G) and diluted with water to 1 liter.

Samples of Examples III and IIIa were applied to spring barley under glasshouse conditions. The compositions were applied at application rates of 3 L/ha and 2.5 L/ha respectively, so as to provide the same application rate of the active components. The dilution was in both cases such as to provide an application rate of 200 L/ha of the dilution. The spring barley was then grown in the glasshouse for 14 days and evaluated for phytotoxicity, expressed as percentage necrosis. The results are shown in the attached table.

| | Rate of product (L/ha) | necrosis after 14 days (%) |
|---|---|---|
| Formulation of Example III | 3 | 3.5 |
| Formulation of Example IIIA Comparative | 2.5 | 12.5 |

This illustrates the advantage of employing a pesticide containing latex formulation.

EXAMPLE IV

Preparation of a mixed formulation of fluroxypyr 1-methyl heptyl ester and bifenox Although fluroxypyr 1-methyl heptyl ester has a melting point of about 56° C., a 3:1 ratio mix of fluroxypyr ester and bifenox has a melting point of 436° C. This was utilized to prepare a low solvent pesticide containing latex dispersion for subsequent admixture with an aqueous suspension concentrate of bifenox.

Fluroxypyr 1-methyl heptyl ester and bifenox (actives E and G) in a 3:1 ratio (24 g) were mixed with surfactants J (12 g) and K (4 g) and then mixed with high shear agitation into a styrene-butyl acrylate latex (latex B) (40 g) and the mixing continued for 30 minutes. Water (20 g) was added. This pesticide containing latex dispersion (42 g) was then added to a commercial bifenox aqueous suspension concentrate (55.4 g) (active G) and diluted with water to 100 ml to produce a formulation containing 50 g/l fluroxypyr acid equivalent and 250 g/L bifenox as a stable formulation.

Comparison of the phytotoxicity potential for fluroxypyr/bifenox formulations (EXAMPLES III AND IV)

Samples of Examples III and IV were applied to barley, cv. lgri, grown under glasshouse conditions, at rates of 200 L/ha. The barley was then grown in the glasshouse for 7 days and evaluated for phytotoxicity, scored according to the European Weed Research Council scoring recommendations for crop injury (listed below).

| | Crop Response | |
|---|---|---|
| Rating | % Crop Injury | Verbal Description |
| 1 | 0 | No reduction or injury |
| 2 | 1.0–3.5 | Very slight discoloration |
| 3 | 3.5–7.0 | More severe but not lasting |
| 4 | 7.0–12.5 | Moderate and more lasting |
| 5 | 12.5–20.0 | Medium and lasting |
| 6 | 20.0–30.0 | Heavy |
| 7 | 30.0–50.0 | Very Heavy |
| 8 | 50.0–99.0 | Nearly destroyed |
| 9 | 100 | Completely destroyed |

The results are as follows:

|  | Rate of product (L/ha) | Crop Injury |
| --- | --- | --- |
| Formulation of Example III | 3 | 3.3 |
| Formulation of Example IV | 3 | 1.5 |

It can be seen that the omission of solvent from the composition, in Example IV, which is made possible by the melting point depression of the mixture, gives rise to even lower phytotoxicity than in Example III.

EXAMPLE V

Preparation of a seed treatment composition containing fenpropimorph, thram and lindane Fenpropimorph (38 g) was added with high shear stirring to a surfactant/latex dispersion produced by mixing 5 g of surfactant A with 38 g of a latex A and water (20 g). The stirring was continued for 15 minutes. This pesticide containing latex dispersion was added to a previously prepared 70% w/w lindane suspension concentrate (780 g). Air-jet milled thiram (75 g) added and Titanium dioxide (30 g) were added, and the mixture was homogenized. 160 g of a 1% xanthan gum concentrate was added and water to 1 liter to yield a stable, very fluid product. This product when applied directly to oil seed rape at a rate of 22 ml/kg seed, produced a much superior coating to the standard commercial product prepared by the use of fenpropimorph as its hydrochloride salt.

EXAMPLE VI

Preparation of a mixed formulation containing myclobutanil, copper oxinate and anthraquinone Myclobutanil (50 g) was dissolved in solvent C (150 g). Surfactant A (5 g) was added to a terpolymer latex (200 g) (latex A) and to this latex/surfactant dispersion was added the previously prepared solution with high shear agitation. The stirring was continued for 20 minutes to produce a stable myclobutanil containing latex.

A suspension concentrate of copper oxinate and anthraquinone was prepared by mixing together under high shear agitation, copper oxinate (67 g), anthraquinone (225 g), surfactant L (30 g), surfactant M (10 g), Ponceau Brilliant 4R (25 g), water (300 g) and xanthan gum (1.5 g). This mixture was then bead-milled to a particle size median of 2.0 microns and the previously prepared pesticide containing latex (400 g) added thereto. The product was diluted to 1 liter with water to produce a stable mixed dispersion. This dispersion was suitable for application to cereal seeds, giving excellent coverage on wheat and barley. A similar product prepared from an emulsion of myclobutanil in solvent C without added latex was physically unstable and did not coat seeds efficiently.

EXAMPLE VII

Preparation of a mixed formulation containing prochloraz and nuarimol

Prochloraz (70 g) was dissolved in solvent C (25 g) and added with high shear agitation to a previously prepared surfactant/latex dispersion of surfactant A (9.0 g) and latex A (100 g). The stirring was continued for 15 minutes to produce a stable prochloraz containing latex.

A suspension concentrate of nuarimol was prepared by mixing together under high shear agitation, nuarimol (38 g), surfactant N (4.0 g), surfactant M (1.0 g), water (300 g) and Xanthan gum (2.0 g). This mixture was then bead-milled to a medium particle size of 2.5 microns and the previously prepared pesticide containing latex (204 g) added thereto. The product was diluted to 1 liter with water to produce a mixed dispersion which was stable on storage for at least 1 month. A similar preparation utilizing an emulsion of prochloraz in Exxate 600 without latex was physically unstable.

EXAMPLE VIII

Preparation of formulation continuing (±)-1-aminopropyl phosphonic acid and prochloraz Prochloraz (70 g) was dissolved in solvent C (25 g) and added with high shear agitation to a previously prepared dispersion of surfactant H (5.0 g) and latex A (100 g). The stirring was continued for 15 minutes to produce a stable prochloraz containing latex. This was added to a 42% w/w solution of Active M as the Potassium salt (55 g) to produce a stable dispersion in this elecrolyte solution. A similar preparation of the prochloraz/Exxate 600 emulsion in the (±)-1-aminopropyl phosphonic acid solution without use of a latex was physically unstable, resulting in gross creaming of the mixture.

EXAMPLE IX

Preparation of a formulation of chlorpyrifos in liquid fertiliser

Chlorpyrifos was dissolved in xylene to produce a 70% w/w solution in xylene. Surfactant H (5 g) was added to 430 g of this 70% w/w chlorpyrifos solution and this oil-phase added to latex A (250 g) with high shear agitation and the stirring continued for 1 hour. The product was then diluted to 1 liter with water. This product was then diluted at 10% v/v into a 9:9:9 NPK solution fertilizer to produce a stable non-creaming product. A similar preparation utilizing an emulsion of chlorpyrifos in xylene without latex was physically unstable, creaming rapidly on being allowed to stand unagitated.

EXAMPLE X

Preparation of a mixed formulation containing myclobutanil, anthraquinone and (±)-1-aminopropyl phosphonic acid Myclobutanil (25 g) was dissolved in Solvent C (50 g) and surfactant D (4.5 g) was added to the solution. This mixture was added with high shear agitation to a latex A (82 g) and water (18 g). The stirring was continued for 10 minutes. This pesticide containing latex dispersion was added to a previously prepared suspension concentrate of anthraquinone prepared by bead milling the following components together to an average particle size of 1.5 microns:

| | |
|---|---:|
| anthraquinone | 120 g |
| Surfactant C | 50 g |
| Surfactant B | 25 g |
| Red pigment | 75 g |
| Silicone antifoam | 5 g |
| Water to | 500 g |

This mixture of myclobutanil and anthraquinone was finally added to a solution of (±)-1-aminopropyl phosphonic acid as the potassium salt (30 g) in water (200 g) and adjusted to one liter with water to produce a stable complex pesticide formulation containing myclobutanil as a latex-stabilised oil phase, anthraquinone as a particulate dispersion in water and (±)-1-amino propyl phosphonic acid (potassium salt) in aqueous solution. Attempts were made to formulate the same active components by conventional techniques, but no other formulation type was found to produce a stable product.

EXAMPLE XI

Preparation of a mixed formulation containing chlorpyrifos-methyl and active N

Chlorpyrifos-methyl (active B) (240 g) was dissolved in solvent B (160 g) and added with high shear agitation to a previously prepared surfactant/latex dispersion of surfactant A (48 g), latex A (240 g) and water (200 g). The stirring was continued for 30 minutes to produce a stable chlorpyrifos-methyl containing latex. To this was added 200 g of a 300 g/L aqueous suspension concentrate of active N prepared by mixing active N (300 g), surfactant E, (25 g), Xanthan gum (1.0 g) and water (approx. 700 g) and bead-milling this mixture to a particle size median of about 1 micron. The product was diluted to 1 liter with water and stirred to homogenize the components, yielding a product containing 240 g/L chlorpyrifos-methyl and 60 g/L of active N. This product was stable on storage, especially showing no physical changes. A similar preparation utilizing an emulsion of active B in solvent B without latex was physically unstable showing gross separation of the phases on storage for one month.

What is claimed is:

1. A water dilutable agricultural pesticidal composition in the form of an aqueous latex dispersion, which dispersion is comprised of a dispersed phase which is comprised of latex particles derived from said latex; a continuous aqueous phase and at least one emulsifying surfactant which is an ethoxylated alcohol, an alkoxylated alcohol, an alkoxylated alkyl phenol, an polyaryl phenol, a half ester sulphosuccinate or a phosphated polyglycol ether and which is compatible with the latex, the latex content of said composition is from 5 to 80 volume weight, said composition further comprises (a) a first active pesticide which is from the group of cypermethrin, amitraz, chlorpyrifos, chlorpyrifos-methyl, fonofos, fenpropimorph, prochloraz, propiconazole, bromoxynil octanoate, myclobutanil, diclofop-methyl, fluazifop-butyl, fluroxypyr-1-methyl heptyl ester, haloyxfop ethoxy-ethyl, haloxyfop ethoxy-methyl, sethoxydim, triclopyr butoxy ethyl ester, a 2-(4-(2-fluoro-4-bromophenoxy)phenoxy propionic acid ester or a resolved isomer thereof or 2,4-( (3-fluoro-5-(trifluoromethyl)-2-pyridinyl)oxy)-phenoxy propanoic acid ester or a resolved isomer thereof which pesticide is present in the composition substantially wholly contained within the first dispersed latex particle phase;

(b) at least one other active component is a second pesticidal component from the group of guazatine, (±)-1-aminopropyl phosphonic acid, bentazone, clopyralid, dicamba, difenzoquat, glyphosate, imazapyr, imazaquin, chlormequat, clofentezine, cyhexatin, gamma-HCH, diflubenzuron, 1-[3,5-dichloro-4-(1,1,2,2-tetrafluoro-ethoxy)phenyl]-3-(2,6-difluorobenzoyl) urea, hexythiazox, anthraquinone, copper oxychloride, copper oxinate, thiabendazole, thiophanate methyl, thiram, bifenox, chlorotoluron, eglinazine, isoproturon, ioxynil, bromoxynil, a biologically active derivative of such active components or a mixture of two or more of such active components or a fertilizer which is physico-chemically, chemically or biologically incompatible with the first pesticidal component and which is present in the composition substantially wholly contained within the said continuous aqueous phase; and (c) said at least one emulsifying surfactant is present in an amount of from 0.1 to 15.0 percent of the total composition.

2. A composition as claimed in claim 1 wherein the said other active component is in the form of an acid, a base, or a salt.

3. A composition as claimed in claim 1 wherein the said other active substance is a water-insoluble solid.

4. A composition as claimed in claim 1 wherein the first pesticidal component is organosoluble, and the second active component is a pesticide which shows increased phytotoxicity when formulated in organic solvents.

5. A composition as claimed in claim 4 wherein the second active component is bifenox.

6. A process for producing an agriculatural composition comprising at least a first active pesticidal component, and at least one other active component which is a second pesticidal component or a fertilizer, the other active component being physico-chemically, chemically or biologically incompatible with the first pesticidal component, which process comprises, forming an emulsion comprising the first pesticidal component and a surfactant, and combining the emulsion with a latex and the second active component so as to form a composition having a continuous aqueous phase, and at least a first dispersed phase, the first dispersed phase containing particles derived from the latex, wherein the said first pesticidal component is present in the composition substantially wholly within the said first dispersed phase, and, wherein the said at least one other active ingredient is present in the continuous aqueous phase or in a second dispersed phase.

7. A method of use of an agricultural composition as claimed in claim 1 which comprises applying the composition to the locus of a pesticidal infestation, or to a locus in which it is desired to prevent pesticidal infestation.

* * * * *